US010287309B2

(12) United States Patent
Guo et al.

(10) Patent No.: US 10,287,309 B2
(45) Date of Patent: May 14, 2019

(54) DISACCHARIDE INTERMEDIATE AND SYNTHESIS METHOD THEREOF

(71) Applicant: Zhejiang Hisun Pharmaceutical Co., Ltd., Zhejiang (CN)

(72) Inventors: Yanghui Guo, Zhejiang (CN); Junhui Zhou, Zhejiang (CN); Qingfeng Cai, Zhejiang (CN); Hegeng Wei, Zhejiang (CN); Hua Bai, Zhejiang (CN); Fei Long, Zhejiang (CN); Yue Zhang, Zhejiang (CN); Yingqiu Wu, Zhejiang (CN)

(73) Assignee: Zhejiang Hisun Pharmaceutical Co., Ltd., Zhejiang (CN)

( * ) Notice: Subject to any disclaimer, the term of this patent is extended or adjusted under 35 U.S.C. 154(b) by 10 days.

(21) Appl. No.: 15/036,390

(22) PCT Filed: Apr. 28, 2014

(86) PCT No.: PCT/CN2014/076359
§ 371 (c)(1),
(2) Date: May 12, 2016

(87) PCT Pub. No.: WO2015/070571
PCT Pub. Date: May 21, 2015

(65) Prior Publication Data
US 2016/0264609 A1 Sep. 15, 2016

(30) Foreign Application Priority Data

Nov. 14, 2013 (CN) .......................... 2013 1 0571340

(51) Int. Cl.
| C07H 11/00 | (2006.01) |
| C07H 17/04 | (2006.01) |
| C07H 1/00 | (2006.01) |
| C07H 3/10 | (2006.01) |
| C07H 13/08 | (2006.01) |
| C07H 13/04 | (2006.01) |

(52) U.S. Cl.
CPC ............... *C07H 11/00* (2013.01); *C07H 1/00* (2013.01); *C07H 3/10* (2013.01); *C07H 13/04* (2013.01); *C07H 13/08* (2013.01); *C07H 17/04* (2013.01)

(58) Field of Classification Search
CPC .............................. C07H 11/00; C07H 17/04
USPC ....................................................... 536/18.1
See application file for complete search history.

(56) References Cited

U.S. PATENT DOCUMENTS

| 4,987,223 A | 1/1991 | Choay et al. |
| 7,541,445 B2 | 6/2009 | Seifert et al. |
| 2005/0065216 A1* | 3/2005 | Bisogno ................. A61K 31/00 514/616 |
| 2012/0083594 A1 | 4/2012 | Hsiao et al. |

FOREIGN PATENT DOCUMENTS

| CN | 103168045 A | 6/2003 |
| JP | H07-267976 A | 10/1995 |
| JP | 2007-112765 A | 5/2007 |
| JP | 2011-093811 A | 5/2011 |
| WO | WO 2012/047174 A1 | 4/2012 |

OTHER PUBLICATIONS

Extended European Search Report for Application No. EP 14861246.8 dated Apr. 6, 2017.
Zhu et al., New principles for glycoside-bond formation. Angew Chem International Edition. 2009;48(11):1900-34.
Kasuya & Hatanaka: "The Chemical Synthesis of a Cyclic Oligosaccharide Derivative with Branching," (1998) Tetrahedron Letters; pp. 9719-9722.
International Search Report, dated Jul. 28, 2014, from corresponding International Application No. PCT/CN2014/076359.
Budesinsky, M et al.: "Syntheses with anhydro sugars. XL. Preparation of β-D-glucopyranosyl derivatives of 1, 6:2, 3-and 1, 6:3, 4-dianhydro-β-D-hexopyranoses and their 1H and 13C NMR spectra", Collection of Czechoslovak Chemical Communications, No. 2, vol. 60, Feb. 28, 1995 (Feb. 28, 1995), pp. 311-322, see p. 312.
Zuurmond, H.M. et al., "Iodonium-promoted glycosylations with phenyl selenoglycosides", Journal of Carbohydrate Chemistry, vol. 12, No. 8, Aug. 31, 1993 (Aug. 31, 1993), pp. 1091-1102, see table 2.
Van Boeckel, C.A.A. et al., "Synthesis of a pentasaccharide corresponding to the antithrombin III binding fragment of heparin", Journal of Carbohydrate Chemistry, vol. 4, No. 3, Jun. 16, 1985 (Jun. 16, 1985), pp. 294-319, see p. 298.
Chinese Office Action for Application No. 201480056049.7, dated May 27, 2017.
Boeckel and Petitou: "The Unique Antithrombin III Binding Domain Heparin: A Lead to New Synthetic Antithrombotics," (1993) Angewandte Chemie; vol. 32 (12) pp. 1671-1818.
Ban and Mrksich: "On-Chip Synthesis and Label-Free Assays of Oligosaccharide Arrays," (2008) Angewandte Chemie; vol. 47; pp. 3396-3399.
Sudibya et al.: "Interfacing Glycosylated carbon-Nanotube-Network Devices with Living Cells to Detect Dynamic Secretion of Biomolecules," (2009) Angewandte Chemie; vol. 48; pp. 2723-2726.

(Continued)

*Primary Examiner* — Shaojia A Jiang
*Assistant Examiner* — Michael C. Henry
(74) *Attorney, Agent, or Firm* — Wolf, Greenfield & Sacks, P.C.

(57) ABSTRACT

The present invention relates to a disaccharide intermediate and a synthesis method thereof, relates to the chemical pharmaceutical field, and more specifically relates to a method for preparing a disaccharide segment of a key intermediate for chemically synthesizing heparin and heparinoid compounds. Disclosed are a new disaccharide intermediate and three methods for synthesizing the disaccharide intermediate, that is, compounds of a formula (4) and glucopyranose protected by different anomeric carbon are made to react in the presence of an active agent, to obtain the disaccharide intermediate. According to the technical solutions of the present invention, synthetic raw materials are easy to obtain, have a mild reaction condition, and are suitable for industrialized production.

7 Claims, No Drawings

(56) References Cited

OTHER PUBLICATIONS

Petitou et al.: "A New Highly Potent, Heparin-Like Pentasaccharide Fragment Containing a Glucose Residue Instead of a Glucosamine," (1991) Bioorganic & Medicidnal Chemistry Letters, vol. 1 (2) pp. 95-98.

Duchaussoy et al.: "The First Total Synthesis of the Antithrombin III Binding Site of Porcine Mucosa Heparin," (1991) Bioorganic & Medicidnal Chemistry Letters, vol. 1 (2) pp. 99-102.

Barrientos et al.: "Gold Glyconanoparticles: Synthetic Polyvalent Ligands Mimicking Glycocalyx-Like Surfaces as Tools for Glycobiological Studies," (2003) Chem. Eur, J.; vol. 9. pp. 1909-192.

Sinay and Jacquinet: "Total synthesis of heparin pentasaccharide fragment having high affinity of antithrombin III," (1985) Carbohydrate Research; vol. 132 pp. C5-C9.

Sail et al.: "Benzoylated ethyl 1-thioglycosides: direct preparation from per-O-benzoylated sugars," (2012) Carbohydrate Research; vol. 357 pp. 47-52.

Kreuzer and Thiem: "Aufbau Von Oligosacchariden MIT Glycosylfluoriden Unter Lewissaure-Katalyse,", (1986) Carbohydrate Research; vol. 149 pp. 347-361.

Houdier and Vottero: "Synthesis of benzylated cycloisomaltotetraose," (1993) Carbohydrate Research; vol. 248 pp. 377-384.

Blattner et al.: "1,3-Dideoxynojirimycin-3-yl glycosides of $\beta$-(1→3)- and $\beta$-(1→6)-linked gluco-oligosaccharides," (2006) Carbohydrate Research; vol. 341 pp. 2115-2125.

Ekholm et al.: "A short semi-synthesis and complete NMR-spectroscopic characterization of the natural occurring lignin glycoside matairesinol 4,4'-di-O-$\beta$-$_D$-diglucoside,"(2006) Carbohydrate Research; vol. 345 pp. 2115-2125.

Balavoine et al.: "Thioglycosides as potential Glycosyl Donors in Electrochemical Glycosylation Reactions. Part 1: Their Preparation and Reactivity Toward Simple Alcohols," (1995) J. Carbohydrate Chemistry; vol. 14(8) pp. 1217-1236.

Zhang et al.: "Synthesis and Applications of a Light-Fluorous Glycosyl Donor," (2009) J. org. Chem.; vol. 74 pp. 2594-2597.

Mbadugha and Menger: "Sugars/Steroids/Sugar Conjugates: Sensitivity of Lipid Binding to Sugar Structure," (2003) Organic Letters; vol. 5(22) pp. 4041-4044.

Ganguli and Coward: "$\alpha$:$\beta$ Selectivity in the synthesis of 3-substituted, 4 methyl umbelliferone glycosides of N-acetyl glucosamine and chitobiose," (2005) Tetrahedron: Asymmetry; vol. 16 pp. 411-424.

Office Action for Japanese Application No. 2016-530127, dated Mar. 1, 2019.

* cited by examiner

DISACCHARIDE INTERMEDIATE AND SYNTHESIS METHOD THEREOF

FIELD OF THE INVENTION

The present invention relates to the chemical pharmaceutical field and in particular to a disaccharide segment intermediate for chemical synthesis of heparin and heparinoid compounds as well as a preparation method thereof.

BACKGROUND OF THE INVENTION

Fondaparinux Sodium is the first synthetic selective inhibitor of thrombin Xa factor, marketed as an anticoagulant drug in 2001, with a chemical name of methyl O-(2-deoxy-2-sulfamido-6-O-sulfo-α-D-glucopyranosyl)-(1→4)-O-(β-D-glucopyranosyluronic acid)-(-1→4)-O-(2-deoxy-2-sulfamido-3,6-di-O-sulfo-α-D-glucopyranosyl)-(1-4)-O-(2-O-sulfo-α-L-idopyranosyluronic acid)-(1→4)-2-deoxy-2-sulfamido-6-O-sulfo-α-D-glucopyranoside decasodium salt, a molecular weight of 1728, and a chemical structure as shown in formula 8:

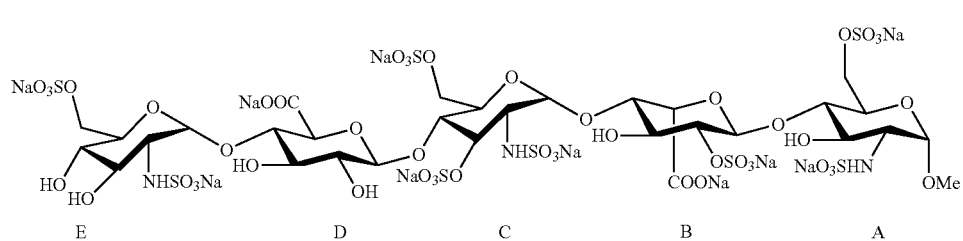

The structure of Fondaparinux Sodium has the following characteristics: Fondaparinux Sodium is formed by sequentially connecting five monosaccharide segments different from each other by an α or β glycosidic bond, with the five monosaccharide segments constituting Fondaparinux Sodium represented from right to left by the letters A, B, C, D and E respectively, wherein segments A, C and E are glucosamine derivatives, segment B is an iduronic acid derivative, and segment D is a glucuronic acid derivative. There are free hydroxyl groups, sulfated hydroxyl groups and sulfated amino groups in the structure of Fondaparinux Sodium, and thus the use of suitable protecting groups in its synthesis design must be taken into consideration in order to meet the following requirements: (1) during the reaction of forming the glycosidic bonds, the protecting groups should be advantageous to form the correct glycosidic bonds in terms of regioselectivity and stereoselectivity; (2) the protecting groups should be selected to allow sulfation in the required position, while other hydroxyl groups are not sulfated; (3) as the synthesis route of the compound is very long, the protecting groups should be selected to be advantageous to improve the efficiency of the reaction, in particular the selectivity and the yield of the glycosylation reaction. In the prior art the synthesis steps of Fondaparinux Sodium are long, the operation is complicated and the total yield is low, being not conducive to industrial-scale production.

The DC disaccharide segment is particularly difficult to synthesize in a total synthesis process of Fondaparinux Sodium. The configuration of the glycosidic bond connecting D segment and C segment is a β configuration, but there is a stereoselectivity problem when the glycosylation reaction for connecting D segment and C segment is carried out, and the reaction may generate α and β glycosylation products simultaneously, resulting in a low yield of the reaction as well as difficult separation and purification of the products. In 1984, Sinay et al (Sinay, P.; Jacquinet, J.; Peittou, M.; Duchaussoy, P.; Lederman, I.; Choay, J. Total synthesis of a heparin pentasaccharide fragment having high affinity for antithrombin. III, *Carbohydrate Research*, 1984, 132, C5-C9) reported the use of a compound of formula 16 and a compound of formula 17 as raw materials in the synthesis of a DC disaccharide segment intermediate compound of formula 18 under the effect of expensive silver salts, wherein the conditions of the glycosylation reaction are harsh, the reaction needs to be carried out for six days, the yield is only 50%, the product is difficult to separate and purify, and the synthesis of the compound of formula 16 as a raw material requires a 14-step chemical reaction; U.S. Pat. No. 4,818,816 also describes the same results.

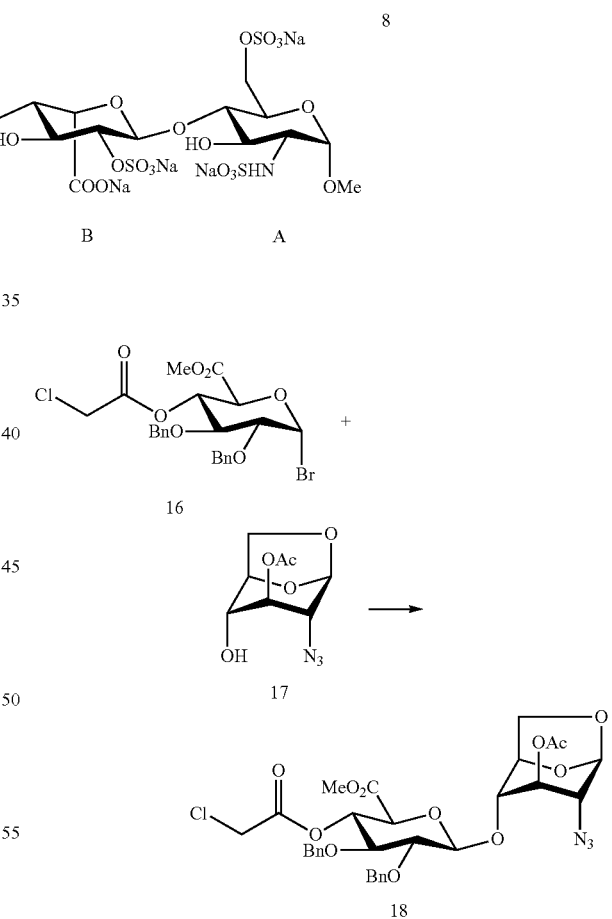

In 1986, Kreuzer, et al. (Kreuzer, M.; Thiem, J. Aufbau von oligosacchariden mit glycosylfluoriden unter lewis-saure-katalyse. *Carbohydrate Research*, 1986, 149, 347-361) reported the use of a fluorinated glycoside compound of formula 19 and a compound of formula 4 in a glycosylation reaction under the effect of equivalent titanium tetrafluoride to synthesize a DC disaccharide segment intermediate compound of formula 12, wherein the yield is only 66%, and the reaction requires the use of large quantities of expensive and highly toxic fluorine-containing reagents.

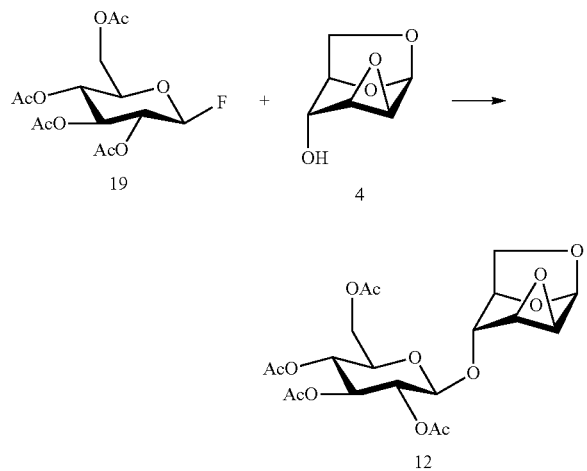

In 1991, Duchaussoy et al (Duchaussoy, P.; Lei, P. S.; Petitou, M.; Synay, P.; Lormeau, J. C.; Choay, J. The first total synthesis of the antithrombin III binding site of porcine mucosa heparin. *Bioorg. Med. Chem. Lett.*, 1991, 1, 99-102) reported the use of a compound of formula 20 and a compound of formula 4 in the synthesis of a DC disaccharide segment intermediate compound of formula 21 under the effect of expensive silver salts, wherein the conditions of the glycosylation reaction are harsh, the yield is only 51%, the reaction has a stereoselectivity of α/β ratio of 1/12, and the product is difficult to separate and purify.

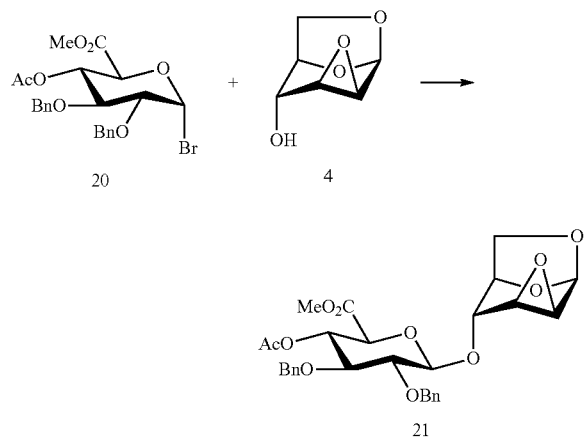

In 1991, Petitou et al (Petitou, M.; Jaurand, G.; Derrien, M.; Duchaussoy, P.; Choay, J. A new, highly potent, heparin-like pentasaccharide for fragment containing a glucose residue instead of a glucosamine. *Bioorg. Med. Chem. Lett.*, 1991, 1, 95-98) reported the use of a cellobiose connected by a β-configuration glycosidic bond in the conversion of functional groups and protecting groups to synthesize a disaccharide segment intermediate, but the synthesis route is long, and the total yield is low. U.S. Pat. No. 7,541,445 describes the glycosylation reaction between a derivative of methyl 2-O-benzoyl-glucuronate and the C segment, wherein the glycosylation reaction is controlled by the effect of neighboring group participation of the benzoyl group to build a β-configuration glycosidic bond in the DC disaccharide segment, followed by the conversion of the derivative of methyl 2-O-benzoyl-glucuronate in the disaccharide segment into a derivative of methyl 2-O-benzyl-glucuronate through a three-step chemical reaction, but these conversions add a number of reaction steps and bring more difficulties to industrial production.

In 1995, Budesinsky et al (Budesinsky, M.; Cerny, M.; Cerny, I.; Samek, S.; Trnka, T. Preparation of β-D-glucopyranosyl derivatives of 1,6;2,3- and 1,6;3,4-dianhydro-β-D-hexopyranoses and their $^1$H and $^{13}$C NMR spectra. *Collect Czech Chem Commun.*, 1995, 60, 311-323) reported the use of a brominated glycoside compound of formula 22 and a compound of formula 4 in a glycosylation reaction to synthesize a DC disaccharide segment compound of formula 12, but the reaction requires the use of large quantities of expensive silver salts as an active agent of the glycosylation reaction.

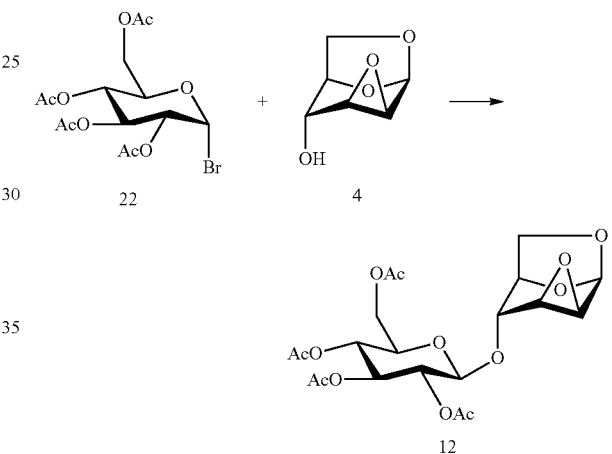

In 1998, Carmelita et al (Kasuya, M. C.; Hatanaka, K.; The chemical synthesis of a cyclic oligosaccharide derivative with branching. *Tetrahedron Lett.*, 1998, 39, 9719-9722) reported the use of a compound of formula 23 and a compound of formula 4 in a glycoside reaction, and since the compound of formula 23 has a benzyl group as a protecting group of the 2-position hydroxy group, the resulting product is a mixture of an α-configuration product, a compound of formula 24 and a β-configuration product, a compound of formula 25 in a ratio of 20:80. The β-configuration product, the compound of formula 25 can be used to synthesize a DC disaccharide segment intermediate, but due to the difficult separation and purification of the above a/β mixture, the method is difficult to apply in mass production.

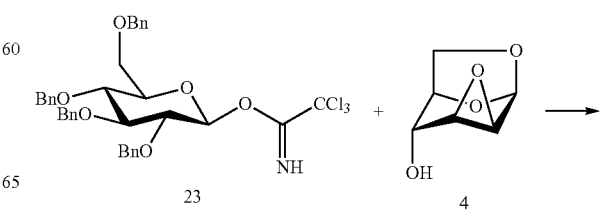

-continued

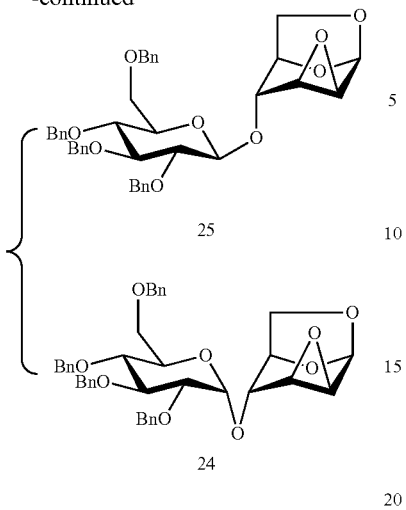

25

24

Chinese Invention Patent Application No. CN201180047939.8 document discloses the use of a compound of formula 26 and a compound of formula 4 in a glycosylation reaction to synthesize a DC disaccharide segment intermediate compound of formula 27, but the synthesis route of the compound of formula 26 as a raw material of the reaction is long and requires the use of expensive and highly toxic reagents, and the acetal protecting group in the compound has low stability against the acidic active agent of the glycosylation reaction, resulting in a low yield and a poor reproducibility of the glycosylation reaction.

In summary, the existing synthetic methods of a DC disaccharide intermediate suffer from multi-step reactions, expensive and highly toxic reagents being used, a low yield of the reaction, difficult separation and purification as well as high cost, and bring a lot of difficulties to large-scale manufacture.

SUMMARY OF THE INVENTION

One of the objects of the present invention is to provide a DC disaccharide intermediate compound of formula 2 as shown below:

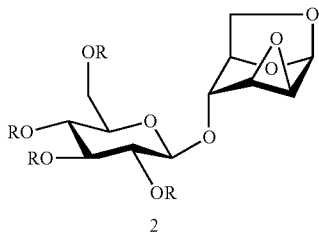

2 wherein R is selected from an alkanoyl group or an aroyl group, and R in the same formula represents the same or different groups;
preferably, R represents the same group;
more preferably, R is selected from an acetyl group or a benzoyl group;
further preferably, R is selected from a benzoyl group.

Another object of the present invention is to provide a method for preparing the compound of formula (2), wherein the following three methods are included: method 1: a glycosylation reaction is carried out between a compound of formula (3) and a compound of formula (4) in the presence of an active agent, to give a compound of formula (2):

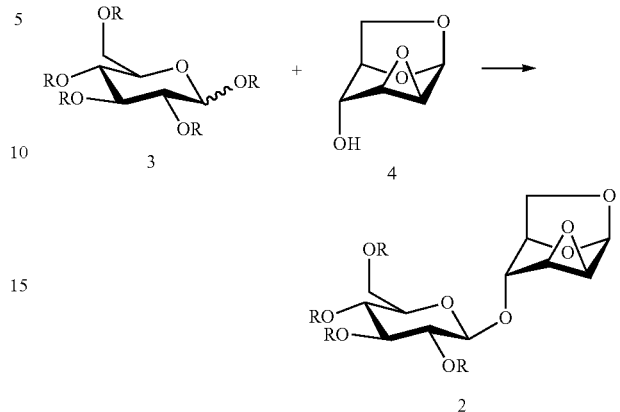

wherein R is selected from an alkanoyl group or an aroyl group, preferably R is selected from an acetyl group or a benzoyl group, and R in the same formula represents the same or different groups; preferably R represents the same group, and further preferably R is benzoyl.

Wherein the anomeric carbon of the compound of formula (3) has a stereo-configuration of α or β or a mixture thereof.

In one embodiment, the active agent is preferably selected from one or more of boron trifluoride-diethyl ether complex, trimethylsilyl triflate, triethylsilyl triflate, t-butyl dimethylsilyl triflate or trifluoromethanesulfonic acid.

In one embodiment, the glycosylation reaction is carried out in the presence of a solvent, the solvent is preferably selected from one or any mixture of ethyl acetate, methyl acetate, N, N-dimethylformamide, diethyl ether, methyl t-butyl ether, tetrahydrofuran, 2-methyl tetrahydrofuran, dioxane, acetonitrile, nitromethane, dichloromethane, 1,2-dichloroethane and toluene.

Method 2: a glycosylation reaction is carried out between a compound of formula (5) and a compound of formula (4) in the presence of an active agent, to give a compound of formula (2):

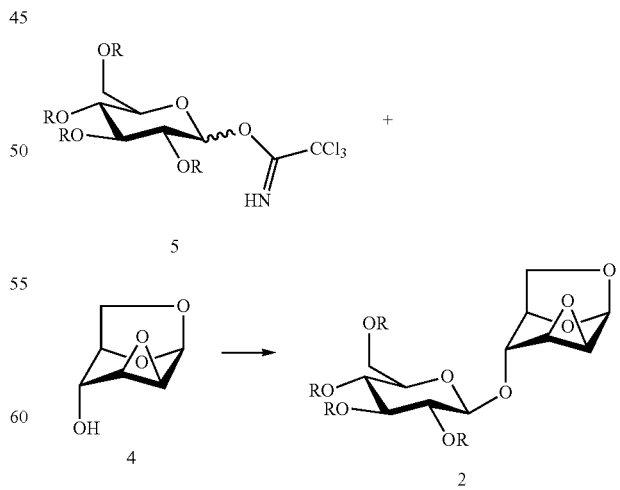

wherein R is selected from an alkanoyl group or an aroyl group, preferably R is selected from an acetyl group or a benzoyl group, and R in the same formula represents the same or different groups; preferably R represents the same group, and further preferably R is benzoyl.

Wherein the anomeric carbon of the compound of formula (5) has a stereo-configuration of α or β or any mixture thereof.

In one embodiment, the active agent is preferably selected from one or more of boron trifluoride-diethyl ether complex, trimethylsilyl triflate, triethylsilyl triflate, t-butyl dimethylsilyl triflate, trifluoromethanesulfonic acid, trifluoromethanesulfonic anhydride, silver triflate, zinc bromide or pyridine p-toluenesulfonate.

In one embodiment, the glycosylation reaction is carried out in the presence of a solvent, the solvent is preferably selected from one or any mixture of ethyl acetate, methyl acetate, N,N-dimethylformamide, diethyl ether, methyl t-butyl ether, tetrahydrofuran, 2-methyl tetrahydrofuran, dioxane, acetonitrile, nitromethane, dichloromethane, 1,2-dichloroethane and toluene.

Method 3: a glycosylation reaction is carried out between a compound of formula (6) and a compound of formula (4) in the presence of an active agent, to give a compound of formula (2):

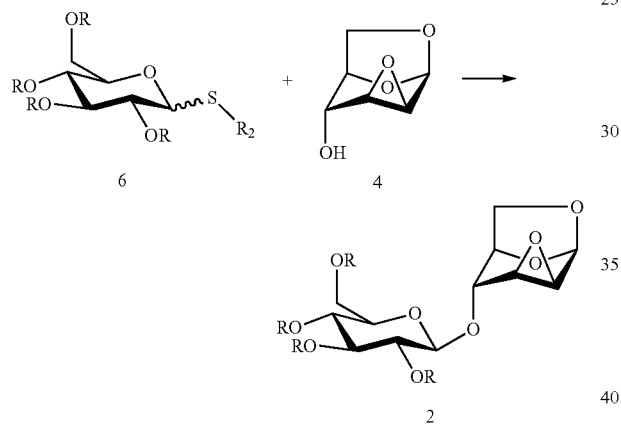

wherein R is selected from an alkanoyl group or an aroyl group, preferably R is selected from an acetyl group or a benzoyl group, R in the same formula represents the same or different groups, preferably R represents the same group, $R_2$ is selected from an alkyl group or an aryl group, preferably $R_2$ is methyl, ethyl, propyl, butyl, isopropyl, phenyl or p-methyl phenyl, and further preferably R is benzoyl.

Wherein the anomeric carbon of the compound of formula (6) has a stereo-configuration of α or β or any mixture thereof.

In one embodiment, the active agent is selected from one or more of N-iodosuccinimide, trimethylsilyl triflate, triethylsilyl triflate, t-butyl dimethylsilyl triflate, trifluoromethanesulfonic acid, silver triflate, methyl triflate, N-bromosuccinimide, methyl triflate, dimethyl methylthio sulfonium triflate, iodonium dicollidine perchlorate or iodonium dicollidine triflate.

In one embodiment, the glycosylation reaction is carried out in the presence of a solvent, the solvent is selected from one or any mixture of ethyl acetate, methyl acetate, N, N-dimethylformamide, diethyl ether, methyl t-butyl ether, tetrahydrofuran, 2-methyl tetrahydrofuran, dioxane, acetonitrile, nitromethane, dichloromethane, 1,2-dichloroethane and toluene.

In a preferred embodiment, the present invention provides a DC disaccharide intermediate compound of formula (1), 1,6:2,3-dianhydro-4-O-(2,3,4,6-tetra-O-benzoyl-β-D-glucopyranosyl)-β-D-mannopyranose as shown below.

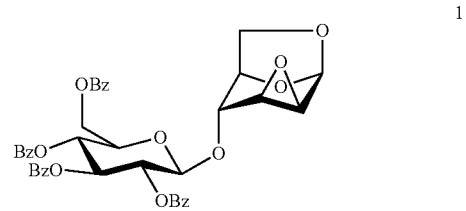

The present invention also provides a method for preparing the compound of formula (1), 1,6:2,3-dianhydro-4-O-(2,3,4,6-tetra-O-benzoyl-β-D-glucopyranosyl)-β-D-mannopyranose: a glycosylation reaction is carried out between a compound of formula (9), penta-O-benzoyl-α/β-D-glucopyranose and a compound of formula (4), 1,6:2,3-dianhydro-β-D-mannopyranose in the presence of an active agent, to give a compound of formula (1), 1,6:2,3-dianhydro-4-O-(2,3,4,6-tetra-O-benzoyl-β-D-glucopyranosyl)-β-D-mannopyranose,

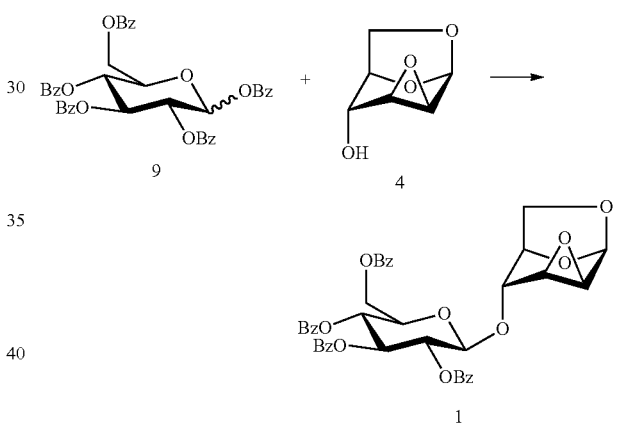

The reaction is carried out in the presence of a solvent, and may be carried out in one or a mixed solvent of ethyl acetate, methyl acetate, N,N-dimethylformamide, diethyl ether, methyl t-butyl ether, tetrahydrofuran, 2-methyl tetrahydrofuran, dioxane, acetonitrile, nitromethane, dichloromethane, 1,2-dichloroethane and toluene, and the active agent is selected from one or more of boron trifluoride-diethyl ether complex, trimethylsilyl triflate, triethylsilyl triflate, t-butyldimethylsilyl triflate or trifluoromethanesulfonic acid.

Wherein the compound of formula 9, penta-O-benzoyl-α/β-D-glucopyranose may be prepared referring to a method in literature (Barrientos, A. G.; Fuente, J. M.; Rojas, T. C.; Fernandez, A.; Penadés, S. Gold glyconanoparticles: synthetic polyvalent ligands mimicking glycocalyx-like surfaces as tools for glycobiological studieds. *Chemistry—A European Journal*, 2003, 9, 1909-1921), and the compound of formula (4), 1,6:2,3-dianhydro-(β-D-mannopyranose may be prepared referring to a method in literature (Ganguli, A. R. S.; Coward, J. K. α:β Selectivity in the synthesis of 3-substituted, 4-methyl umbelliferone glycosides of N-acetyl glucosamine and chitobiose. *Tetrahedron: Asymmetry*, 2005, 16, 411-424).

In another preferred embodiment, the present invention also provides another method for preparing the compound of formula (1), 1,6:2,3-dianhydro-4-O-(2,3,4,6-tetra-O-benzoyl-β-D-glucopyranosyl)-β-D-mannopyranose: a glycosylation reaction is carried out between a compound of formula (10), 2,3,4,6-tetra-O-benzoyl-α/β-D-glucopyranosyl trichloroacetonitrile imidate and a compound of formula (4), 1,6:2,3-dianhydro-β-D-mannopyranose in the presence of an active agent, to give a compound of formula (1), 1,6:2,3-dianhydro-4-O-(2,3,4,6-tetra-O-benzoyl-β-D-glucopyranosyl)-β-D-mannopyranose,

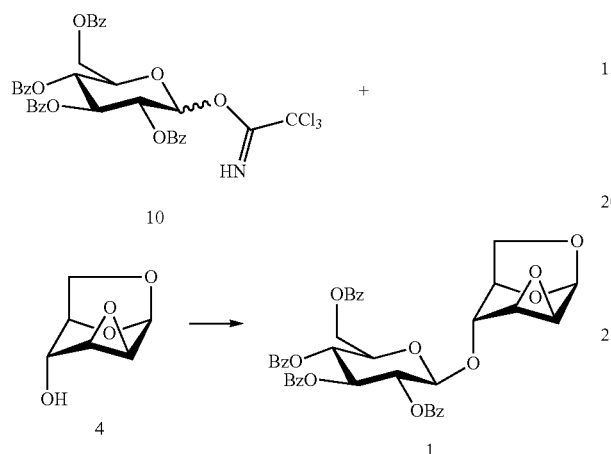

The reaction is carried out in the presence of a solvent, and may be carried out in one or a mixed solvent of ethyl acetate, methyl acetate, N,N-dimethylformamide, diethyl ether, methyl t-butyl ether, tetrahydrofuran, 2-methyl tetrahydrofuran, dioxane, acetonitrile, nitromethane, dichloromethane, 1,2-dichloroethane and toluene, and the active agent is selected from one or more of boron trifluoride-diethyl ether complex, trimethylsilyl triflate, triethylsilyl triflate, t-butyldimethylsilyl triflate, trifluoromethanesulfonic acid, trifluoromethanesulfonic anhydride, silver triflate, zinc bromide or pyridine p-toluenesulfonate.

Wherein the compound of formula (10), 2,3,4,6-tetra-O-benzoyl-α/β-D-glucopyranosyl trichloroacetonitrile imidate may be prepared referring to a method in literature (Barrientos, A. G.; Fuente, J. M.; Rojas, T. C.; Fernandez, A.; Penadés, S. Gold glyconanoparticles: synthetic polyvalent ligands mimicking glycocalyx-like surfaces as tools for glycobiological studieds. *Chemistry—A European Journal*, 2003, 9, 1909-1921; Mbadugha, B. N. A.; Menger, F. M. Sugar/steroid/sugar conjugates: sensitivity of lipid binding to sugar structure. *Organic Letters*, 2003, 5, 4041-4044; Ekholm, F. S.; Eklund, P.; Leino, R. A short semi-synthesis and complete NMR-spectroscopic characterization of the naturally occurring lignan glycoside matairesinol 4,4'-di-O-β-D-diglucoside. *Carbohydrate Research*, 2010, 345, 1963-1967).

In another preferred embodiment, the present invention also provides another method for preparing the compound of formula (1), 1,6:2,3-dianhydro-4-O-(2,3,4,6-tetra-O-benzoyl-β-D-glucopyranosyl)-β-D-mannopyranose: a glycosylation reaction is carried out between a compound of formula 11 and a compound of formula (4), 1,6:2,3-dianhydro-(β-D-mannopyranose in the presence of an active agent, to give a compound of formula (1), 1,6:2,3-dianhydro-4-O-(2,3,4,6-tetra-O-benzoyl-(β-D-glucopyranosyl)-β-D-mannopyranose,

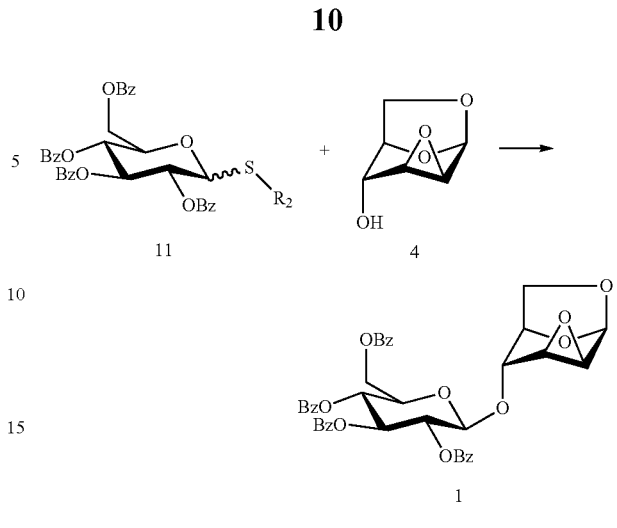

Wherein $R_2$ in the compound of formula 11 is selected from an alkyl group or an aryl group, and $R_2$ is preferably selected from methyl, ethyl, propyl, butyl, isopropyl, phenyl, p-methylphenyl and the like.

The reaction is carried out in the presence of a solvent, and may be carried out in one or a mixed solvent of ethyl acetate, methyl acetate, N,N-dimethylformamide, diethyl ether, methyl t-butyl ether, tetrahydrofuran, 2-methyl tetrahydrofuran, dioxane, acetonitrile, nitromethane, dichloromethane, 1,2-dichloroethane and toluene, and the active agent is selected from one or more of N-iodosuccinimide, trimethylsilyl triflate, triethylsilyl triflate, t-butyl dimethylsilyl triflate, trifluoromethanesulfonic acid, silver triflate, methyl triflate, N-bromosuccinimide, methyl triflate, dimethyl methylthio sulfonium triflate, iodonium dicollidine perchlorate or iodonium dicollidine triflate.

Wherein the compound of formula 11 may be prepared referring to a method in literature (Balavoine, G.; Berteina, S.; Gref, A.; Fischer, J.; Lubineau, A. Thioglycosides as potential glycosyl donors in electrochemical glycosylation reactions. part 1: their preparation and reactivity toward simple alcohols. *Journal of Carbohydrate Chemistry*, 1995, 14, 1217-1236; Sail, D.; Kovac, P. Benzoylated ethyl 1-thio-glycosides: direct preparation from per-O-benzoylated sugars. *Carbohydrate Research*, 2012, 357, 47-52).

In another preferred embodiment, the present invention also provides a method for preparing a compound of formula (7), 1,6:2,3-dianhydro-4-O-(β-D-glucopyranosyl)-(β-D-mannopyranose: the compound of formula (1), 1,6:2,3-dianhydro-4-O-(2,3,4,6-tetra-O-benzoyl-(β-D-glucopyranosyl)-β-D-mannopyranose is subjected to a hydrolysis reaction under the effect of a basic reagent, to remove four benzoyl groups and give a compound of formula 7:

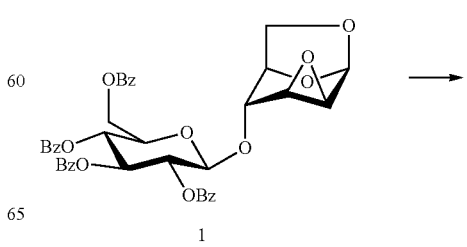

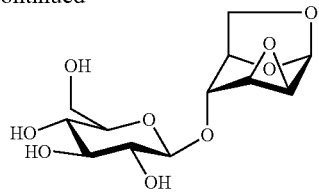

Wherein the basic reagent is selected from sodium hydroxide, potassium hydroxide, sodium methoxide, sodium ethoxide, triethylamine, ammonia and hydrazine, and the reaction solvent is selected from water, methanol, ethanol, or a mixture thereof.

In another preferred embodiment, the present invention also provides a method for preparing a compound of formula (12), 1,6:2,3-dianhydro-4-O-(2,3,4,6-tetra-O-acetyl-β-D-glucopyranosyl)-β-D-mannopyranose: a glycosylation reaction is carried out between a compound of formula 13, penta-O-acetyl-α/β-D-glucopyranose and a compound of formula 4, 1,6:2,3-dianhydro-(β-D-mannopyranose in the presence of an active agent, to give a compound of formula (12), 1,6:2,3-dianhydro-4-O-(2,3,4,6-tetra-O-acetyl-β-D-glucopyranosyl)-β-D-mannopyranose,

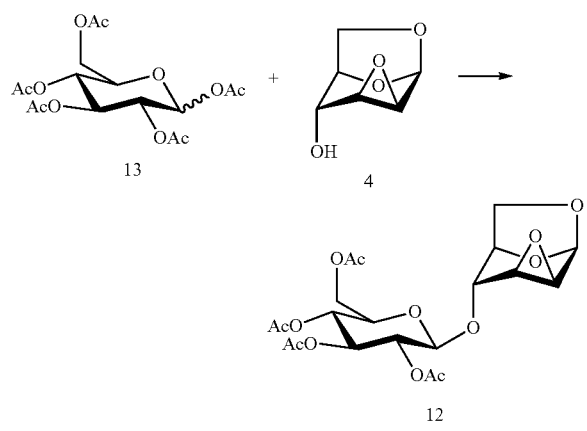

The reaction is carried out in the presence of a solvent, and may be carried out in one or a mixed solvent of ethyl acetate, methyl acetate, N,N-dimethylformamide, diethyl ether, methyl t-butyl ether, tetrahydrofuran, 2-methyl tetrahydrofuran, dioxane, acetonitrile, nitromethane, dichloromethane, 1,2-dichloroethane and toluene, and the active agent is selected from one or more of boron trifluoride-diethyl ether complex, trimethylsilyl triflate, triethylsilyl triflate, t-butyldimethylsilyl triflate, trifluoromethanesulfonic acid, trifluoromethanesulfonic anhydride, silver triflate, zinc bromide or pyridine p-toluenesulfonate.

Wherein the compound of formula 13, penta-O-acetyl-α/β-D-glucopyranose may be prepared referring to a method in literature (Sudibya, H. G.; Ma, J.; Dong, X.; Ng, S.; Li, L. J.; Liu, X. W.; Chen, P. Interfacing glycosylated carbon-nanotube-network devices with living cells to detect dynamic secretion of biomolecules. *Angewandte Chemie*, International Edition, 2009, 48, 2723-2726).

In another preferred embodiment, the present invention also provides a method for preparing the compound of formula (12), 1,6:2,3-dianhydro-4-O-(2,3,4,6-tetra-O-acetyl-β-D-glucopyranosyl)-β-D-mannopyranose: a glycosylation reaction is carried out between a compound of formula (14), 2,3,4,6-tetra-O-acetyl-α/β-D-glucopyranosyl trichloroacetonitrile imidate and a compound of formula (4), 1,6:2,3-dianhydro-(β-D-mannopyranose in the presence of an active agent, to give a compound of formula (12), 1,6:2,3-dianhydro-4-O-(2,3,4,6-tetra-O-acetyl-β-D-glucopyranosyl)-β-D-mannopyranose,

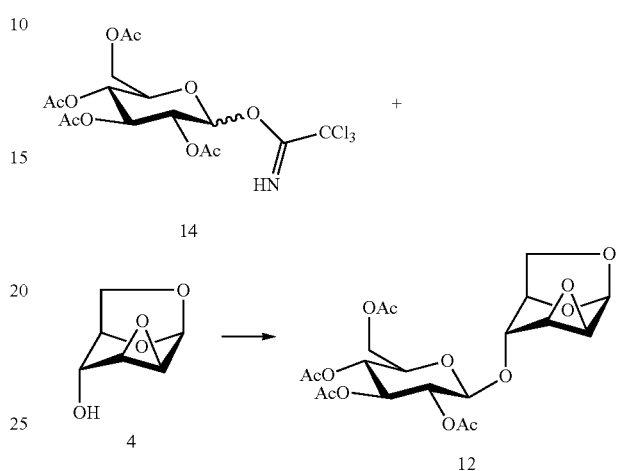

The reaction is carried out in the presence of a solvent, and may be carried out in one or a mixed solvent of ethyl acetate, methyl acetate, N,N-dimethylformamide, diethyl ether, methyl t-butyl ether, tetrahydrofuran, 2-methyl tetrahydrofuran, dioxane, acetonitrile, nitromethane, dichloromethane, 1,2-dichloroethane and toluene, and the active agent is selected from one or more of boron trifluoride-diethyl ether complex, trimethylsilyl triflate, triethylsilyl triflate, t-butyldimethylsilyl triflate, trifluoromethanesulfonic acid, trifluoromethanesulfonic anhydride, silver triflate, zinc bromide or pyridine p-toluenesulfonate.

Wherein the compound of formula (14), 2,3,4,6-tetra-O-acetyl-α/β-D-glucopyranosyl trichloroacetonitrile imidate may be prepared referring to a method in literature (Ban, L.; Mrksich, M. On-chip synthesis and label-free assays of oligosaccharide arrays. *Angewandte Chemie*, International Edition, 2008, 47, 3396-3399; Blattner, R.; Furneaux, R. H.; Pakulski, Z. 1,3-Dideoxynojirimycin-3-yl glycosides of β-(1→3)- and β-(1→6)-linked gluco-oligosaccharides. *Carbohydrate Research*, 2006, 341, 2115-2125).

In another preferred embodiment, the present invention also provides another method for preparing the compound of formula (12), 1,6:2,3-dianhydro-4-O-(2,3,4,6-tetra-O-acetyl-β-D-glucopyranosyl)-β-D-mannopyranose: a glycosylation reaction is carried out between a compound of formula 15 and a compound of formula (4), 1,6:2,3-dianhydro-β-D-mannopyranose in the presence of an active agent, to give a compound of formula (12), 1,6:2,3-dianhydro-4-O-(2,3,4,6-tetra-O-acetyl-β-D-glucopyranosyl)-β-D-mannopyranose,

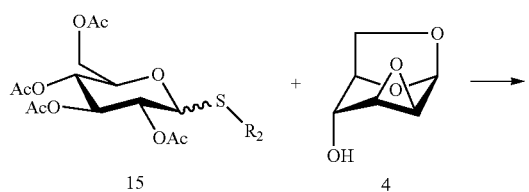

13

-continued

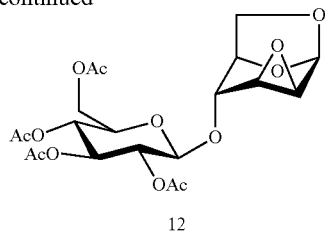

12

Wherein $R_2$ in the compound of formula 15 is selected from an alkyl group or an aryl group, and $R_2$ is preferably selected from methyl, ethyl, propyl, butyl, isopropyl, phenyl, p-methylphenyl and the like.

The reaction is carried out in the presence of a solvent, and may be carried out in one or a mixed solvent of ethyl acetate, methyl acetate, N,N-dimethylformamide, diethyl ether, methyl t-butyl ether, tetrahydrofuran, 2-methyl tetrahydrofuran, dioxane, acetonitrile, nitromethane, dichloromethane, 1,2-dichloroethane and toluene, and the active agent is selected from one or more of N-iodosuccinimide, trimethylsilyl triflate, triethylsilyl triflate, t-butyl dimethylsilyl triflate, trifluoromethanesulfonic acid, silver triflate, methyl triflate, N-bromosuccinimide, methyl triflate, dimethyl methylthio sulfonium triflate, iodonium dicollidine perchlorate or iodonium dicollidine triflate.

The compound of formula 15 may be prepared referring to a method in literature (Zhang, F.; Zhang, W.; Zhang, Y.; Curran, D. P.; Liu, G. Synthesis and applications of a light-fluorous glycosyl donor. *Journal of Organic Chemistry*, 2009, 74, 2594-2597; Houdier, S.; Vottero, P. J. A. Synthesis of benzylated cycloisomaltotetraose. *Carbohydrate Research*, 1993, 248, 377-384).

The compound of formula (7), 1,6:2,3-dianhydro-4-O-(β-D-glucopyranosyl)-(β-D-mannopyranose and the compound of formula (12), 1,6:2,3-dianhydro-4-O-(2,3,4,6-tetra-O-acetyl-β-D-glucopyranosyl)-β-D-mannopyranose may be applied to the synthesis of heparinoid compounds such as Fondaparinux Sodium and the like referring to a method in literature (Boeckel, C. A. A.; Beetz, T.; Vos, J. N.; Jong, A. J. M.; Aelst, S. F. V.; Bosch, R. H.; Mertens, J. M. R.; Vlugt, F. A.; Synthesis of a pentasaccharide corresponding to the antithrombin III binding fragment of heparin. *Journal of Carbohydrate Chemistry*, 1985, 4, 293-321; Petitou, M.; Jaurand, G.; Derrien, M.; Duchaussoy, P.; Choay, J. A new, highly potent, heparin-like pentasaccharide for fragment containing a glucose residue instead of a glucosamine. *Bioorg. Med. Chem. Lett.*, 1991, 1, 95-98; Boeckel, C. A. A.; Petitou, M. *Angew. Chem. Int. Ed. Engl.*, 1993, 32, 1671-1690.), and the chemical conversion process is as follows:

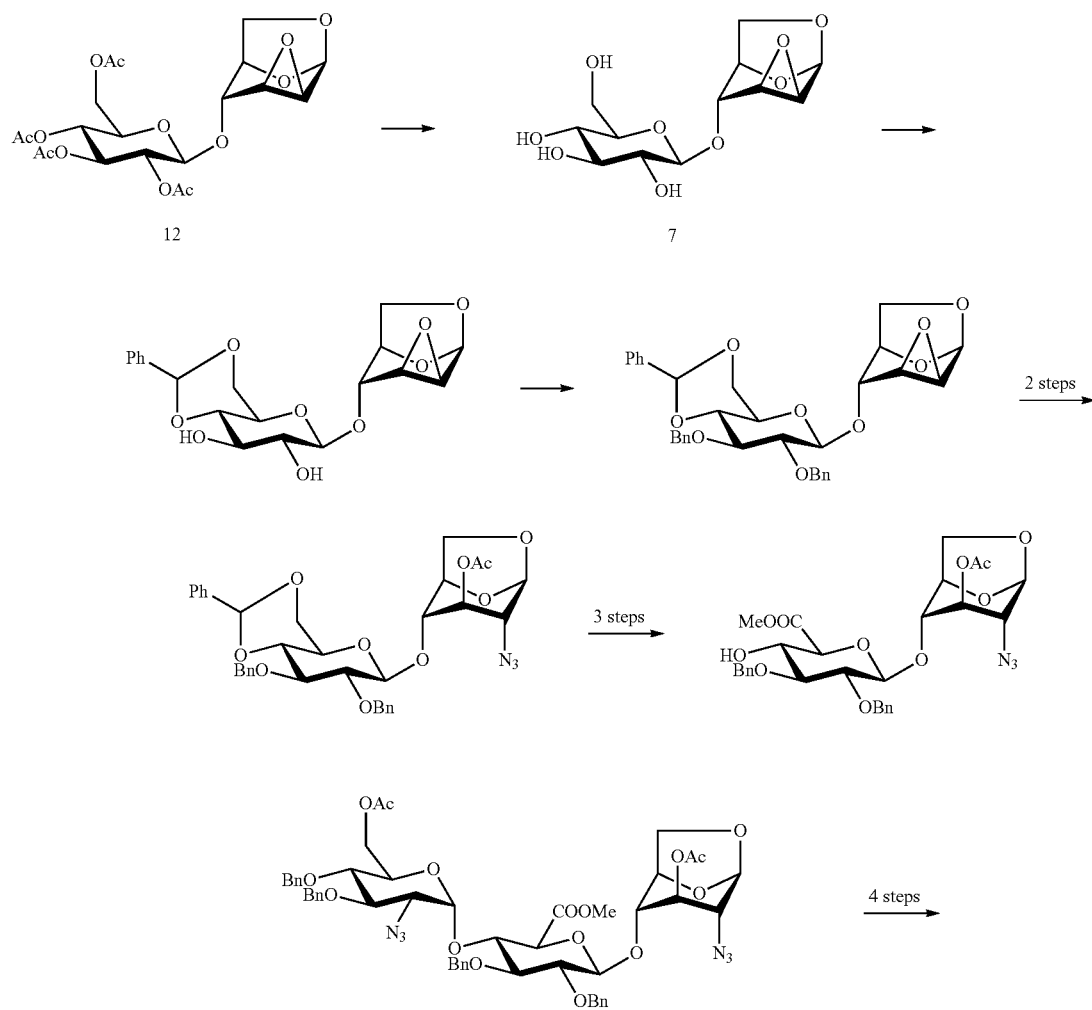

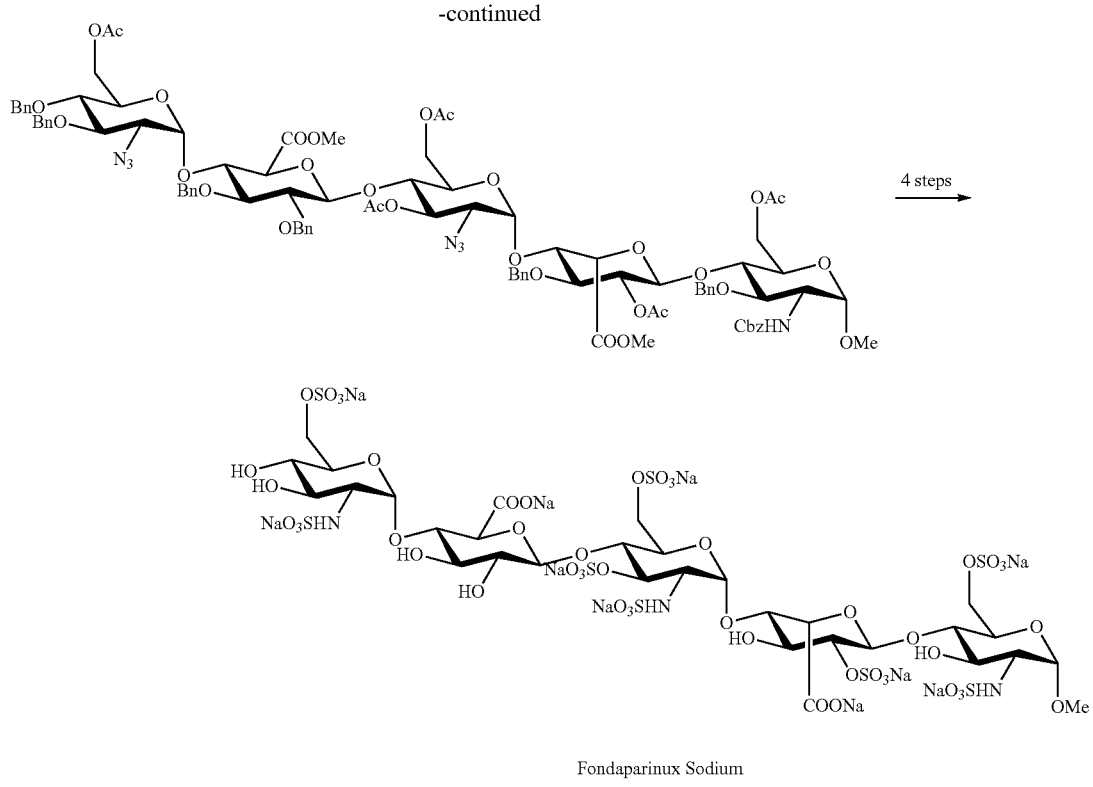

Fondaparinux Sodium

The present invention provides a DC disaccharide intermediate and a preparation method thereof, and meanwhile also provides the use of such disaccharide intermediates in the preparation of heparin and heparinoid compounds.

Heparinoid compounds according to the present invention are a kind of compounds having a structure similar to heparin, including heparin pentasaccharide.

Preferably, the heparinoid compounds are heparin pentasaccharide.

Further preferably, the heparin pentasaccharide is Fondaparinux Sodium.

The present technical solutions has at least one of the following advantages:

The present invention overcomes the deficiencies and disadvantages in the prior art in that the reaction conditions are mild and the reagents used are cheap and less toxic; and, the glycosylation reactions used in the present invention have a high yield and good stereoselectivity, all the reaction products are exclusively β-configuration products without observing the generation of α-configuration products, and the separation and purification of the products may also be carried out by recrystallization; the present invention provides a straightforward process route, a simple operation process and low cost, and the intermediate may be purified by a recrystallization method, which is suitable for industrial-scale manufacture. Wherein, the reactions for synthesizing the compound of formula 12 have a high stereoselectivity and the separation and purification are simple, which is better than the methods disclosed in the current literature; the reactions for synthesizing the compound of formula 1 have a high stereoselectivity, simple post-treatment and a high yield.

DETAILED EMBODIMENTS

Example 1

Preparation of 1,6:2,3-dianhydro-4-O-(2,3,4,6-tetra-O-acetyl-β-D-glucopyranosyl)-β-D-mannopyranose

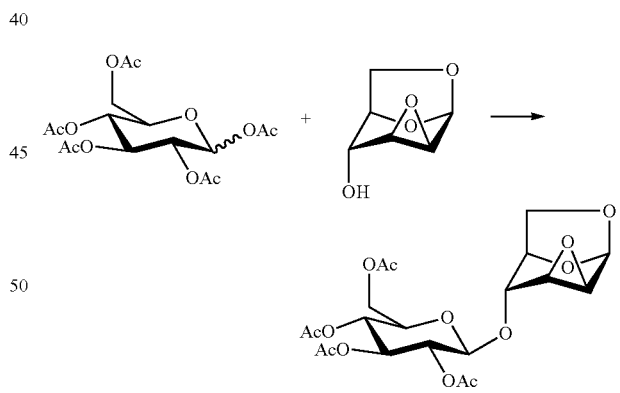

4.6 g of penta-O-acetyl-α/β-D-glucopyranose and 1.0 g of 1,6:2,3-dianhydro-β-D-mannopyranose were dissolved in 100 ml of dichloromethane and cooled to minus 20 degrees, into which 1.9 ml of boron trifluoride-diethyl ether was added; then the reaction system was naturally warmed to room temperature and stirred until the reaction was completed, into which a small amount of triethylamine was added to quench the reaction; the reaction system was washed with saturated sodium bicarbonate solution and divided, and the organic phase was dried with anhydrous sodium sulfate and concentrated under reduced pressure; the crude product was purified by flash column chromatography to give a product, 2.1 g of—1,6:2,3-dianhydro-4-O-(2,3,4,6-tetra-O-acetyl-β-D-glucopyranosyl)-β-D-mannopyranose with a yield of 64%.

1H NMR (400 MHz, CDCl3): δ 5.69 (d, J=2.8 Hz, 1H), 5.24 (t, J=9.6 Hz, 1H), 5.10 (t, J=9.6 Hz, 1H), 5.03 (t, J=8.4 Hz, 1H), 4.77 (d, J=8.0 Hz, 1H), 4.43 (d, J=5.2 Hz, 1H), 4.26 (dd, J, =12.4 Hz, z=5.2 Hz, 1H), 4.16 (d, J=12.4 Hz, 1H), 3.93 (s, 1H), 3.77-3.71 (m, 3H), 3.47 (s, 1H), 3.30 (d, J=2.4 Hz, 1H), 2.09 (s, 3H), 2.07 (s, 3H), 2.04 (s, 3H), 2.02 (s, 3H); 13C NMR (100 MHz, CDCl3): δ 170.5, 170.2, 169.3, 169.2, 100.2, 97.6, 74.7, 72.6, 72.1, 71.8, 71.2, 68.2, 65.6, 61.8, 54.5, 48.1, 20.7, 20.6, 20.5, 20.5; ESI-MS m/z 475.2 [M+H$^+$].

Example 2

Preparation of 1,6:2,3-dianhydro-4-O-(2,3,4,6-tetra-O-benzoyl-β-D-glucopyranosyl)-β-D-mannopyranose

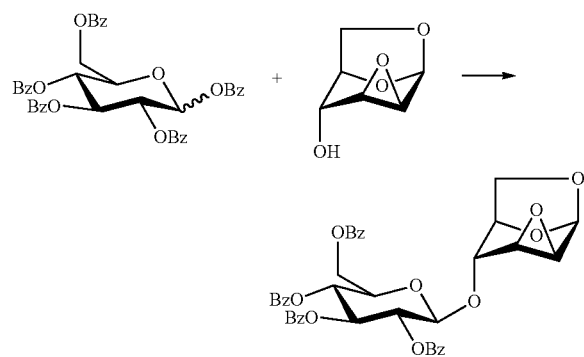

7.3 g of penta-O-benzoyl-α/β-D-glucopyranose and 1.0 g of 1,6:2,3-dianhydro-(β-D-mannopyranose were dissolved in 100 ml of dichloromethane and cooled to minus 20 degrees, into which 1.3 ml of boron trifluoride-diethyl ether was added; then the reaction system was naturally warmed to room temperature and stirred until the reaction was completed, into which a small amount of triethylamine was added to quench the reaction; the reaction system was washed with saturated sodium bicarbonate solution and divided, and the organic phase was dried with anhydrous sodium sulfate and concentrated under reduced pressure; the crude product was purified by flash column chromatography to give a product, 2.4 g of 1,6:2,3-dianhydro-4-O-(2,3,4,6-tetra-O-benzoyl-β-D-glucopyranosyl)-β-D-mannopyranose with a yield of 47%.

$^1$H NMR (400 MHz, CDCl$_3$): δ 8.01 7.26 (m, 20H), 5.94 (t, J=9.6 Hz, 1H), 5.68 (t, J=9.6 Hz, 1H), 5.64 (d, J=2.8 Hz, 1H), 5.58 (dd, J$_1$=9.6 Hz, z=8.0 Hz, 1H), 5.17 (d, J=8.0 Hz, 1H), 4.69 (dd, J, =12 Hz, J$_2$=2.8 Hz, 1H), 4.49 (dd, J$_1$=12 Hz, J$_2$=5.6 Hz, 1H), 4.42 (d, J=6 Hz, 1H), 4.22 (m, 1H), 3.97 (s, 1H), 3.60 (m, 2H), 3.41 (t, J=3.2 Hz, 1H), 3.34 (d, J=3.2 Hz, 1H); $^{13}$C NMR (100 MHz, CDCl3): δ 166.1, 165.8, 165.2, 165.0, 133.6, 133.4, 133.3, 133.2, 129.9, 129.8, 129.7, 129.6, 129.5, 129.1, 128.7, 128.6, 128.5, 128.3, 100.8, 97.5, 75.1, 72.8, 72.6, 72.1, 71.8, 69.6, 65.9, 62.9, 54.6, 48.1; ESI-MS m/z: 722.9 [M+H$^+$].

Example 3

Preparation of 1,6:2,3-dianhydro-4-O-(2,3,4,6-tetra-O-acetyl-β-D-glucopyranosyl)-β-D-mannopyranose

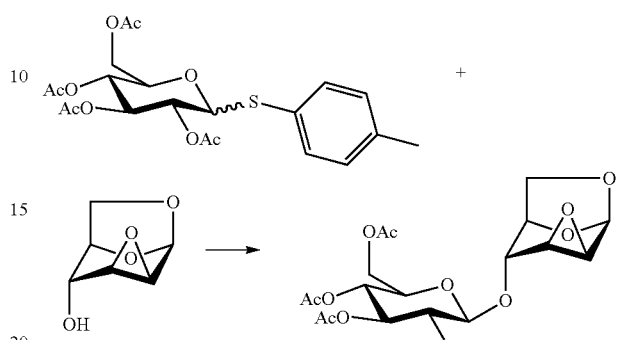

3.5 g of p-methylphenyl 2,3,4,6-tetra-O-acetyl-1-thio-α/β-D-glucopyranoside and 1.0 g of 1,6:2,3-dianhydro-β-D-mannopyranose were dissolved in 100 ml of dichloromethane, into which 5.0 g of 4 Å molecular sieves was added. The reaction solution was cooled to minus 30 degrees, into which 1.7 g of iodosuccinimide and 0.07 ml of trifluoromethanesulfonic acid were added, and the reaction solution was naturally warmed to 0 degree and reacted. After the reaction was completed, a saturated aqueous solution of sodium bicarbonate was added to quench the reaction, and the reaction system was divided; the organic phase was washed with a 1.0 M aqueous solution of sodium thiosulfate and divided, and the separated organic phase was dried with anhydrous sodium sulfate and concentrated under reduced pressure; the crude product was purified by flash column chromatography to give a product, 2.7 g of—1,6:2,3-dianhydro-4-O-(2,3,4,6-tetra-O-acetyl-β-D-glucopyranosyl)-β-D-mannopyranose with a yield of 82%.

Example 4

Preparation of 1,6:2,3-dianhydro-4-O-(2,3,4,6-tetra-O-acetyl-β-D-glucopyranosyl)-β-D-mannopyranose

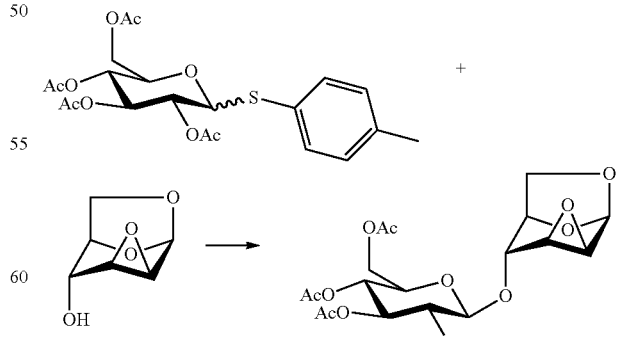

3.8 g of p-methylphenyl 2,3,4,6-tetra-O-acetyl-1-thio-α/β-D-glucopyranoside and 1.0 g of 1,6:2,3-dianhydro-(β-D-mannopyranose were dissolved in 100 ml of dichloromethane, into which 5.0 g of 4 Å molecular sieves was added. The reaction solution was cooled to minus 30 degrees, into which 3.1 g of iodosuccinimide and 0.25 ml of trimethylsilyl triflate were added, and the reaction solution was naturally warmed to 0 degree and reacted. After the reaction was completed, a saturated aqueous solution of sodium bicarbonate was added to quench the reaction, and the reaction system was divided; the organic phase was washed with a 1.0 M aqueous solution of sodium thiosulfate and divided, and the separated organic phase was dried with anhydrous sodium sulfate and concentrated under reduced pressure; the crude product was purified by flash column chromatography to give a product, 3.0 g of 1,6:2,3-dianhydro-4-O-(2,3,4,6-tetra-O-acetyl-β-D-glucopyranosyl)-β-D-mannopyranose with a yield of 91%.

Example 5

Preparation of 1,6:2,3-dianhydro-4-O-(2,3,4,6-tetra-O-benzoyl-β-D-glucopyranosyl)-β-D-mannopyranose

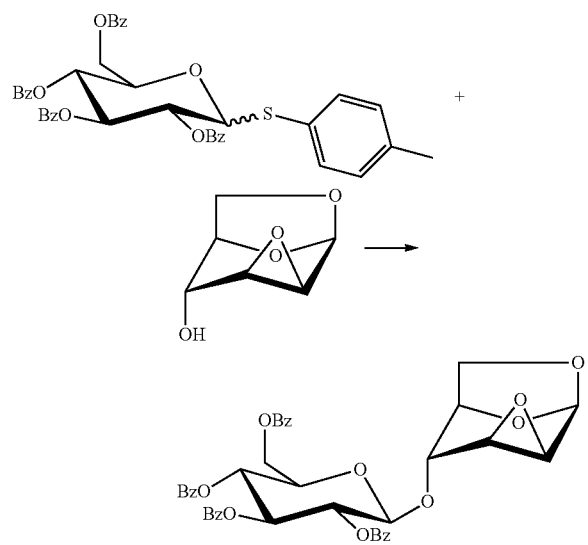

5.8 g of p-methylphenyl 2,3,4,6-tetra-O-benzoyl-1-thio-α/β-D-glucopyranoside and 1.0 g of 1,6:2,3-dianhydro-(β-D-mannopyranose were dissolved in 100 ml of dichloromethane, into which 5.0 g of 4 Å molecular sieves was added. The reaction solution was cooled to minus 30 degrees, into which 1.7 g of iodosuccinimide and 0.07 ml of trifluoromethanesulfonic acid were added, and the reaction solution was naturally warmed to 0 degree and reacted. After the reaction was completed, a saturated aqueous solution of sodium bicarbonate was added to quench the reaction, and the reaction system was divided; the organic phase was washed with a 1.0 M aqueous solution of sodium thiosulfate and divided, and the separated organic phase was dried with anhydrous sodium sulfate and concentrated under reduced pressure; the crude product was purified by flash column chromatography to give a product, 4.6 g of 1,6:2,3-dianhydro-4-O-(2,3,4,6-tetra-O-benzoyl-β-D-glucopyranosyl)-β-D-mannopyranose with a yield of 92%.

Example 6

Preparation of 1,6:2,3-dianhydro-4-O-(2,3,4,6-tetra-O-benzoyl-β-D-glucopyranosyl)-β-D-mannopyranose

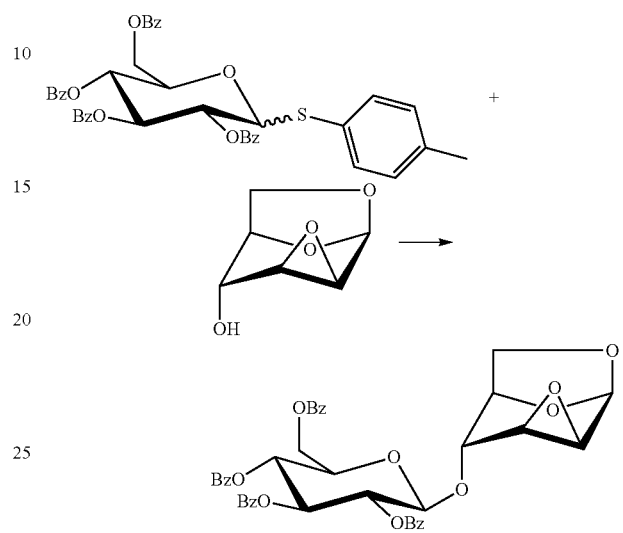

2.9 g of p-methylphenyl 2,3,4,6-tetra-O-benzoyl-1-thio-α/β-D-glucopyranoside and 0.54 g of 1,6:2,3-dianhydro-β-D-mannopyranose were dissolved in 90 ml of toluene, into which 3.0 g of 4 Å molecular sieves was added. The reaction solution was cooled to minus 30 degrees, into which 1.7 g of iodosuccinimide and 0.07 ml of trifluoromethanesulfonic acid were added, and the reaction solution was naturally warmed to 0 degree and reacted. After the reaction was completed, a saturated aqueous solution of sodium bicarbonate was added to quench the reaction, and the reaction system was divided; the organic phase was washed with a 1.0 M aqueous solution of sodium thiosulfate and divided, and the separated organic phase was dried with anhydrous sodium sulfate and concentrated under reduced pressure; the crude product was purified by flash column chromatography to give a product, 2.1 g of 1,6:2,3-dianhydro-4-O-(2,3,4,6-tetra-O-benzoyl-β-D-glucopyranosyl)-β-D-mannopyranose with a yield of 78%.

Example 7

Preparation of 1,6:2,3-dianhydro-4-O-(2,3,4,6-tetra-O-acetyl-β-D-glucopyranosyl)-β-D-mannopyranose

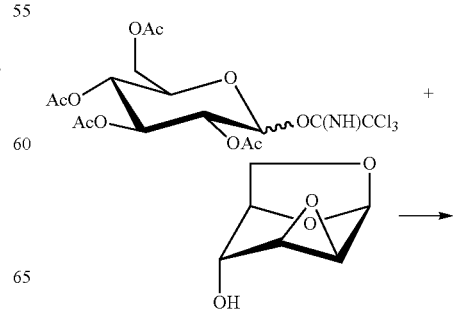

-continued

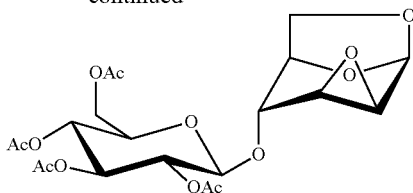

5.9 g of 2,3,4,6-tetra-O-acetyl-α/β-D-glucopyranoside trichloroacetonitrile imidate and 1.2 g of 1,6:2,3-dianhydro-(β-D-mannopyranose were dissolved in 100 ml of dichloromethane. The reaction solution was cooled to minus 20 degrees, into which 1.48 ml of boron trifluoride-diethyl ether was added. After the reaction was completed, a saturated aqueous solution of sodium bicarbonate was added to quench the reaction, and the reaction system was divided; the organic phase was washed with a 1.0 M aqueous solution of sodium thiosulfate and divided, and the separated organic phase was dried with anhydrous sodium sulfate and concentrated under reduced pressure; the crude product was purified by flash column chromatography to give a product, 3.5 g of 1,6:2,3-dianhydro-4-O-(2,3,4,6-tetra-O-acetyl-β-D-glucopyranosyl)-β-D-mannopyranose with a yield of 89%.

Example 8

Preparation of 1,6:2,3-dianhydro-4-O-(2,3,4,6-tetra-O-acetyl-β-D-glucopyranosyl)-β-D-mannopyranose

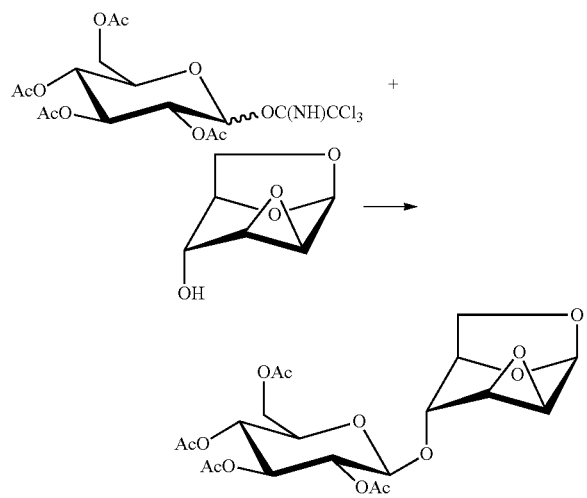

3.2 g of 2,3,4,6-tetra-O-acetyl-α/β-D-glucopyranosidyl trichloroacetonitrile imidate and 0.85 g of 1,6:2,3-dianhydro-(β-D-mannopyranose were dissolved in 70 ml of acetonitrile. The reaction solution was cooled to minus 20 degrees, into which 0.7 ml of boron trifluoride-diethyl ether was added. After the reaction was completed, a saturated aqueous solution of sodium bicarbonate was added to quench the reaction, and the reaction system was divided; the organic phase was washed with a 1.0 M aqueous solution of sodium thiosulfate and divided, and the separated organic phase was dried with anhydrous sodium sulfate and concentrated under reduced pressure; the crude product was purified by flash column chromatography to give a product, 1.73 g of 1,6:2,3-dianhydro-4-O-(2,3,4,6-tetra-O-acetyl-β-D-glucopyranosyl)-β-D-mannopyranose with a yield of 62%.

Example 9

Preparation of 1,6:2,3-dianhydro-4-O-(2,3,4,6-tetra-O-acetyl-β-D-glucopyranosyl)-β-D-mannopyranose

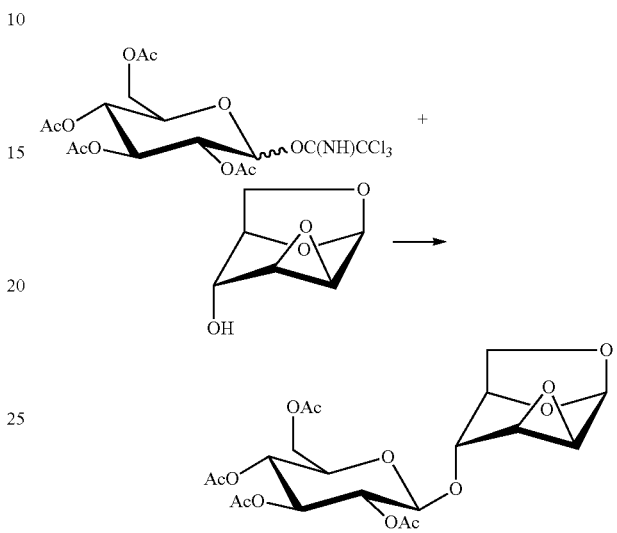

5.9 g of 2,3,4,6-tetra-O-acetyl-α/β-D-glucopyranosidyl trichloroacetonitrile imidate and 1.2 g of 1,6:2,3-dianhydro-(β-D-mannopyranose were dissolved in 100 ml of dichloromethane, into which 5.0 g of 4 Å molecular sieves was added. The reaction solution was cooled to minus 20 degrees, into which 0.25 ml of trimethylsilyl triflate was added. After the reaction was completed, a saturated aqueous solution of sodium bicarbonate was added to quench the reaction, and the reaction system was divided; the organic phase was washed with a 1.0 M aqueous solution of sodium thiosulfate and divided, and the separated organic phase was dried with anhydrous sodium sulfate and concentrated under reduced pressure; the crude product was purified by flash column chromatography to give a product, 3.4 g of 1,6:2,3-dianhydro-4-O-(2,3,4,6-tetra-O-acetyl-β-D-glucopyranosyl)-β-D-mannopyranose with a yield of 86%.

Example 10

Preparation of 1,6:2,3-dianhydro-4-O-(2,3,4,6-tetra-O-benzoyl-β-D-glucopyranosyl)-β-D-mannopyranose

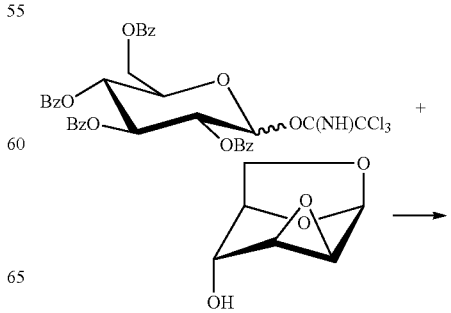

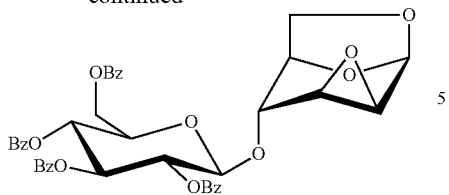

5.0 g of 2,3,4,6-tetra-O-benzoyl-α/β-D-glucopyranosidyl trichloroacetonitrile imidate and 0.65 g of 1,6:2,3-dianhydro-(β-D-mannopyranose were dissolved in 100 ml of dichloromethane. The reaction solution was cooled to minus 20 degrees, into which 0.83 ml of boron trifluoride-diethyl ether was added. After the reaction was completed, a saturated aqueous solution of sodium bicarbonate was added to quench the reaction, and the reaction system was divided; the organic phase was washed with a 1.0 M aqueous solution of sodium thiosulfate and divided, and the separated organic phase was dried with anhydrous sodium sulfate and concentrated under reduced pressure; the crude product was purified by flash column chromatography to give a product, 2.9 g of 1,6:2,3-dianhydro-4-O-(2,3,4,6-tetra-O-benzoyl-β-D-glucopyranosyl)-β-D-mannopyranose with a yield of 89%.

Example 11

Preparation of 1,6:2,3-dianhydro-4-O-(2,3,4,6-tetra-O-benzoyl-β-D-glucopyranosyl)-β-D-mannopyranose

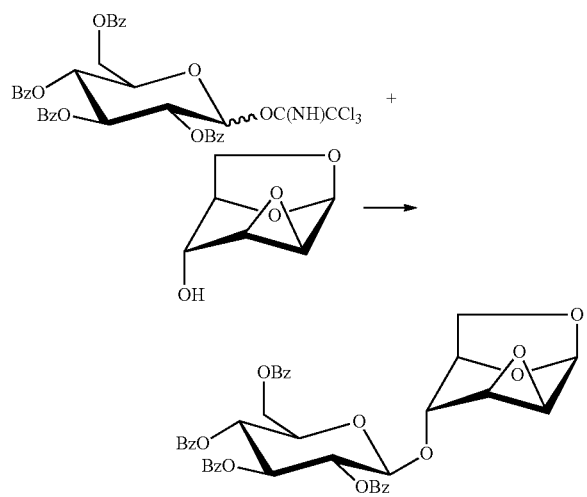

7.0 g of 2,3,4,6-tetra-O-benzoyl-α/β-D-glucopyranosidyl trichloroacetonitrile imidate and 1.0 g of 1,6:2,3-dianhydro-β-D-mannopyranose were dissolved in 100 ml of dichloromethane. The reaction solution was cooled to minus 20 degrees, into which 0.2 g of trifluoromethanesulfonic acid was added. After the reaction was completed, a saturated aqueous solution of sodium bicarbonate was added to quench the reaction, and the reaction system was divided; the organic phase was dried with anhydrous sodium sulfate and concentrated under reduced pressure; the crude product was purified by flash column chromatography to give a product, 4.3 g of 1,6:2,3-dianhydro-4-O-(2,3,4,6-tetra-O-benzoyl-β-D-glucopyranosyl)-β-D-mannopyranose with a yield of 86%.

Example 12

Preparation of 1,6:2,3-dianhydro-4-O-(β-D-glucopyranosyl)-β-D-mannopyranose

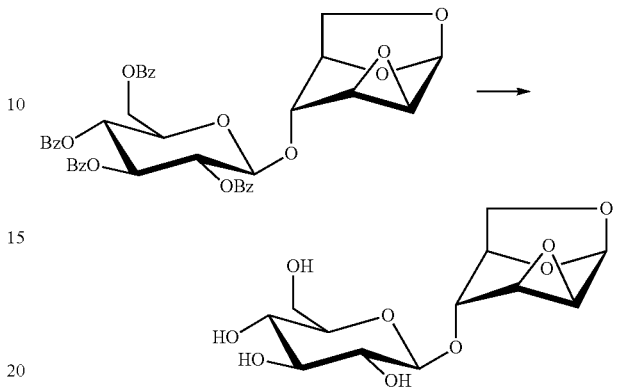

1.0 g of 1,6:2,3-dianhydro-4-O-(2,3,4,6-tetra-O-benzoyl-β-D-glucopyranosyl)-β-D-mannopyranose was mixed with 20 ml of anhydrous methanol, into which 0.04 g of sodium methoxide was added; the reaction system was stirred at room temperature until the reaction was completed. Dilute hydrochloric acid was added to quench the reaction, and the reaction system was concentrated under reduced pressure. The crude product was purified by flash column chromatography to give a product, 0.39 g of 1,6:2,3-dianhydro-4-O-(β-D-glucopyranosyl)-β-D-mannopyranose with a yield of 92%.

$^1$H NMR (400 MHz, D$_2$O): δ 5.85 (d, J=2.4 Hz, 1H), 4.70 (d, J=7.6 Hz, 1H), 4.67 (m, 1H), 4.23 (s, 1H), 3.91 (dd, J, =12.8 Hz, J$_2$=2.0 Hz, 1H), 3.78-3.71 (m, 3H), 3.65 (t, J=3.6 Hz, 1H), 3.53-3.42 (m, 4H), 3.33 (m, 1H); $^{13}$C NMR (100 MHz, D$_2$O): δ 102.3, 97.1, 76.0, 75.6, 74.0, 73.0, 72.1, 69.5, 65.3, 60.6, 54.2, 48.4; ESI-MS m/z: 329.1 [M+Na$^+$].

Example 13

Preparation of 1,6:2,3-dianhydro-4-O-(β-D-glucopyranosyl)-β-D-mannopyranose

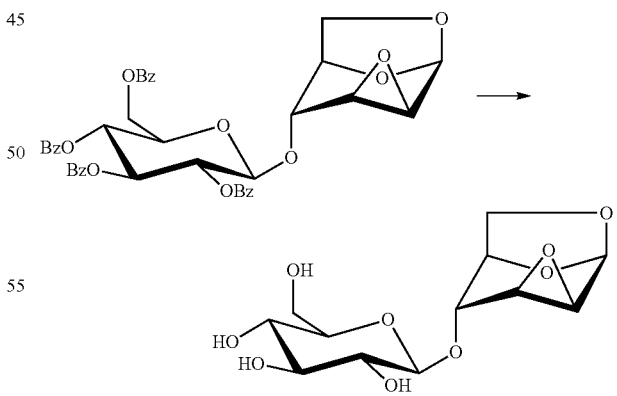

1.0 g of 1,6:2,3-dianhydro-4-O-(2,3,4,6-tetra-O-benzoyl-β-D-glucopyranosyl)-β-D-mannopyranose was dissolved in a mixed solution of 10 ml anhydrous methanol and 10 ml tetrahydrofuran, into which 10 ml of a 1.0 M aqueous solution of sodium hydroxide was added, and the reaction system was stirred until the reaction was completed. Dilute hydrochloric acid was added to quench the reaction, and the reaction system was concentrated under reduced pressure.

The crude product was purified by flash column chromatography to give a product, 0.35 g of 1,6:2,3-dianhydro-4-O-(β-D-glucopyranosyl)-(β-D-mannopyranose with a yield of 83%.

The invention claimed is:

1. A process for preparing a compound of formula (2), comprising a step of glycosylation reaction between a compound of formula (3) and a compound of formula (4) in the presence of an active agent:

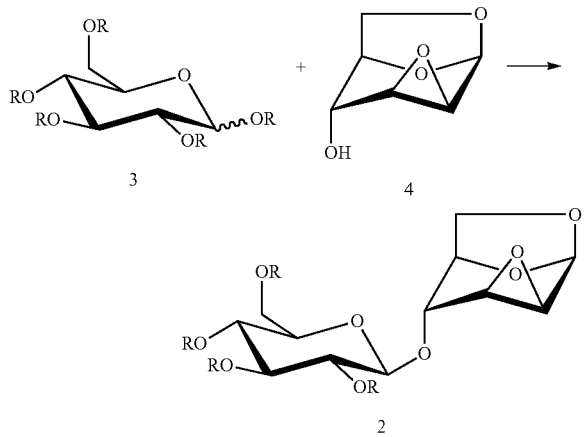

wherein:

R is an alkanoyl group or an aroyl group, and R in the same formula represents the same groups; and the active agent is selected from one or more of boron trifluoride-diethyl ether complex, trimethylsilyl triflate, triethylsilyl triflate, t-butyl dimethylsilyl triflate, and trifluoromethanesulfonic acid.

2. The process according to claim 1, wherein the anomeric carbon of the compound of formula (3) has a stereo-configuration of α or β or a mixture thereof.

3. The process according to claim 1, wherein the glycosylation reaction is carried out in the presence of a solvent.

4. The process according to claim 1, wherein R is an acetyl group or a benzoyl group.

5. The process according to claim 1, wherein R is benzoyl.

6. The process according to claim 3, wherein the solvent is ethyl acetate, methyl acetate, N,N-dimethylformamide, ethyl ether, methyl t-butyl ether, tetrahydrofuran, 2-methyl tetrahydrofuran, dioxane, acetonitrile, nitromethane, dichloromethane, 1,2-dichloroethane, or toluene, or a mixture thereof.

7. The process according to claim 1, wherein R is an acetyl group.

* * * * *